United States Patent [19]
Plymale

[11] 3,997,504
[45] Dec. 14, 1976

[54] COMPOSITION AND METHOD FOR TREATING TEETH

[76] Inventor: Richard W. Plymale, 1480 Griffin Road, Davison, Mich. 48423

[22] Filed: Feb. 20, 1975

[21] Appl. No.: 551,461

Related U.S. Application Data

[62] Division of Ser. No. 130,438, April 1, 1971, Pat. No. 3,882,600.

[52] U.S. Cl. .............................. 260/42.27; 106/35; 526/245; 526/279
[51] Int. Cl.² .............. C08F 214/18; C08F 230/02
[58] Field of Search .......... 260/80 PS, 86.1 R, 960, 260/973, 42.27; 32/15; 106/35

[56] References Cited
UNITED STATES PATENTS

| | | | |
|---|---|---|---|
| 2,495,108 | 1/1950 | Kosolopoff | 260/973 |
| 2,614,116 | 10/1952 | Lange et al. | 260/960 |
| 2,674,590 | 4/1954 | Zenftman | 260/973 |
| 2,712,548 | 7/1955 | Hood | 260/973 |
| 2,714,100 | 7/1955 | Toy et al. | 260/86.1 R |
| 2,871,263 | 1/1959 | Short | 260/80 PS |
| 3,105,064 | 9/1963 | Kramer et al. | 260/80 PS |
| 3,540,126 | 11/1970 | Chang et al. | 260/42.27 |

*Primary Examiner*—Donald E. Czaja
*Assistant Examiner*—S. M. Person
*Attorney, Agent, or Firm*—Reising, Ethington, Barnard, Perry & Brooks

[57] ABSTRACT

In accordance with the invention there is provided a method, and a composition for the practice of the method, for repairing tooth or bone structure wherein there is applied to the tooth or bone tissue a composition comprising a polymerized or polymerizable organic phosphoryl monofluoride thereby to attain a strong bond to the tooth or bone tissue.

9 Claims, No Drawings

COMPOSITION AND METHOD FOR TREATING TEETH

This application is a division of application Ser. No. 130,438, filed Apr. 1, 1971, and now U.S. Pat. No. 3,882,600.

This invention relates to a method and composition for treating diseased, decayed or damaged tooth or bone structure and, more particularly for repairing tooth or bone structure by application of a composition which assures the attainment of a strong bond with the tissue. The invention has particular utility for the repair or filling of tooth cavities and hence will be described in its details principally in conjunction therewith though, as will be mentioned hereinafter, the invention finds numerous other uses in the dental and medical sciences.

When caries is discovered in a tooth, the dentist removes the diseased tooth substance, cleans out the cavity in the tooth formed by such removal, and then shapes the cavity to the best form to receive and retain a filling, all based on accepted principles well known in the art of dentistry. At the present state of the art, none of the dental restorative or filling materials used have a significant degree of chemical or physical adhesion to the hard tooth tissues and hence retention of the filling material is dependent upon mechanical locking. This frequently requires the removal of healthy tooth structure for providing recesses in the tooth to better assure mechanical retention of the filling material. The filling materials presently in use, because they do not provide a strong and permanent bond to the hard tooth tissues, frequently permit bacteria to reach under the filling after a period of time and hence result in further decay at the tooth-filling interface.

It is a principal object of the present invention to provide an improved process and composition for the restoration of diseased or otherwise damaged or defective teeth which assures an excellent leak-resistant bond between the filling material and the hard tooth tissue thereby to solve the aforesaid problem. Another and attendant object of the invention is the provision of a composition and method for lining a tooth cavity to assure an excellent bond and seal to the tooth structure and also to the body of filler material used to fill the lined cavity.

Briefly, these objects are accomplished, in accordance with the preferred embodiment of the invention, by lining the cavity, after the diseased tissue has been removed and after the cavity has been thoroughly cleansed, with a composition comprising a polymerizable organic phosphoryl monofluoride. More specifically, in the preferred embodiment the material used for the lining comprises an organic ester of monofluorophorophosphoric acid wherein the organic radical is unsaturated, i.e., contains at least one carbon-to-carbon double bond, whereby it is polymerizable by addition polymerization. Hence, the lining material has the formula

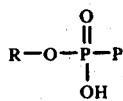

wherein R is an unsaturated addition polymerizable group. As will be seen from the more detailed description set forth hereinafter, the preferred liner incorporates a methacrylic group or groups to provide the polymerization though other unsaturated addition polymerizable groups may be used if desired. It should be pointed out that by the term "polymerizable" is not meant that the compound is necessarily entirely in monomeric form at the time of application of the composition to the tooth since it is within the purview of the invention that the organic phosphoryl monofluoride be in polymeric form, or at least partially polymerized, prior to application to the tooth and the invention as herein described is intended to comprehend such embodiments. However, in the preferred embodiment the organic phosphoryl monofluoride, though not necessarily totally in monomeric form, is in a form whereby there can be polymerization, or further polymerization, in situ, on the tooth after application of the liner. Hence, in the preferred embodiment the liner material as initially applied, or after application thereof, also includes a small but effective amount of a catalyst to induce the desired polymerization, in situ, after the lining has been applied. Further, and as will also be described in greater detail hereinafter, the liner material, in its preferred embodiments, also contains additional organic polymer or polymerizable compound and finely divided solid material as coloring pigment or to contribute other or additional desirable physical characteristics.

Other objects, features and advantages of the invention will appear more clearly from the following detailed description thereof and, in this regard, and as alluded to above, it should be understood that whereas the invention is described herein principally in connection with the filling of tooth cavities, it additionally finds utility in other dental and medical work and procedures. For example, the composition and process can be used on external tooth surfaces so that orthodontists can provide improved attachment of appliances. Further, the invention enables periodontists to use improved splinting techniques and prosthodontists to obtain better results in the cementing of abutments. Still further, the composition can be used by general practitioners to provide increased cavity prevention by using the composition for the filling of developmental pits and fissures in teeth which, if not treated, could eventually result in cavities. Also, because bone tissue is quite similar to tooth tissue, the present invention can find utility by orthopedic surgeons for the repair of diseased, damaged or deformed bone structures. Moreover, the unsaturated organic phosphoryl monofluorides can find utility as intermediate or primer coatings to provide a better bonding of acrylic or the like materials to metal surfaces.

At present, the strong trend in dentistry is to discontinue the use of dental amalgam for the filling of tooth cavities due to its lack of tooth color, which renders it unattractive. In place of dental amalgam it has become the trend to use organic resins, or more accurately, mixtures of organic resins modified with chemically inert powder material, so as to closely match the color of the tooth filling to that of the tooth. The filling resins most commonly used in dentistry at the present time are methylmethacrylate monomer, with lesser or greater amounts of related compatible monomeric or dimeric materials, together with varying amounts of powder fillers, as aforesaid, sometimes treated with silanes, the general characteristics of which are described in U.S. Pat. Nos. 3,066,112, 3,194,783 and 3,503,128. As has already been mentioned, however, the chief difficulty with these resinous filling compositions, just as was and is a difficulty with dental amalgam, is that of attaining a really strong leak-proof bond between the filling and the tooth. The present invention, in its most preferred embodiment and application, contemplates not the total replacement of the currently used resinous filling compositions but rather the supplementation thereof by first lining the tooth cavity with the composition and process of this invention and then using the aforedescribed currently marketed resinous filling compositions, or other resinous compositions, to fill the remainder and generally the bulk of the cavity. In effect, therefore, the liner functions as a transition layer at the interface of the filling with the tooth which layer provides a superior bond and seal with the tooth structure and also a good bond with the remainder of the filling composition which fills the bulk of the cavity. As indicated above, but to elaborate on the point, the liner which functions as this transitional layer can, if desired, be applied with the polymerizable organic phosphoryl monofluoride already in a substantially fully polymerized state - this by dissolving the liner composition, i.e. the polymeric constituents thereof, in a suitable solvent to provide the desired viscosity whereby, after application, the solvent rapidly evaporates leaving the solid constituents of the liner bonded to the tooth tissue. However, when, as in the preferred embodiment, the organic phosphoryl monofluoride of the liner is in a nonpolymerized, or not totally polymerized, state as the liner is applied to the tooth, there can, by way of the subsequent polymerization thereof in situ, be copolymerization and cross-linking between the liner and the polymerizable ingredients of the remainder of the tooth filling whereby the resulting transitional layer provides the ultimate in bond strength not only with the tooth tissue but also with the composition forming the bulk of the filling.

As indicated above, the embodiment of the liner composition of this invention which is most preferred, on the basis of results to date, contains at least one and preferably a plurality of methacrylic groups as the addition polymerizable sites. Illustrative is glycerol dimethacrylate monoester of monofluorophoshoric acid:

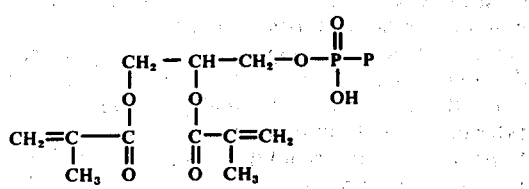

Typical of other organic phosphoryl monofluorides incorporating a methacrylate group and serving well for the practice of the invention is ethylene glycol monomethylacrylate monofluorophosphate

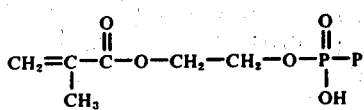

However, numerous other addition polymerizable organic radicals can be used in place of the methacrylic group, examples of which can best be given with reference to the method which can be used for making the ester.

Reference is here made to U.S. Pat. No. 2,712,548, issued July 5, 1955 to Archie Hood, which patent describes a method which can be used for manufacture of organic esters of monofluorophosphoric acid. The reaction is as follows:

Here, for the preparation of the ester for practice of the present invention, R is an organic radical containing aliphatic unsaturation thereby to provide an addition polymerizable compound. Hence, the reaction can be described as the esterification of the fluorophoshoric acid with an aliphatic unsaturated monohydric alcohol, and preferably one wherein the unsaturation is present in the form of one or more vinyl type groups. The alcohol used can be a simple, unsaturated monohydric aliphatic alcohol of which the following are examples:
Allyl Alcohol
Methallyl Alcohol (i.e. 2-methyl-2-propen-1-ol.)
3-Buten-1-ol.
1-Hexen-3-ol.
4 Methyl-3 Penten-2-ol.

The alcohol used can, and on the basis of my work to date preferably should, contain acrylate or methacrylate groups, of which the following are examples:
1. 2 hydroxy ethyl methacrylate (or acrylate, i.e. the acrylate can be used instead of the methacrylate) glycol mono methacrylate (or acrylate)
2. glycerol dimethacrylate
3. 1,2,6-triol-dimethacrylate
4. tri-methylol propane-dimethacrylate The alcohol used can contain other chemical groups or elements, an example being cinnamic alcohol (i.e. 3-phenyl -2 propen-1-ol). For preparation of the addition polymerizable phosphoryl monofluoride the compound used for the esterification reaction need not be an alcohol but it must, of course, react as or like an alcohol insofar as esterification reactions are concerned. An example of such a compound is glycidyl methacrylate. Hence such compounds are intended to be comprehended by the term "alcohol" in my description of the manner of preparation of the phosphoryl monofluoride esters.

Based on theory and results to date, it is generally preferred that the aliphatic chain not contain more than 8 carbon atoms. Further, and as indicated above, preferred are the aliphatic or aromatic monohydric alcohols containing one or more substituted polymerizable groups, ideally methacrylate or acrylate groups.

It should be noted that the above description and in all the examples given of the "R" radical of the phosphoryl monofluoride, only carbon, hydrogen and oxygen atoms are present. Investigation to date indicates that such esters of monofluorophosphoric acid are non-toxic, and though I do not wish to infer that other atoms cannot, for the practice of the invention, be present in the organic radical, I prefer, on the basis of work to date, that the organic radical of the monofluorophosphoric acid contain no atoms other than hydrogen, oxygen and carbon simply on the grounds that the presence of other atoms could conceivably raise toxicity problems.

As indicated previously, the esters of the monofluorophosphoric acid for the practice of the present invention can be prepared in accordance with the teachings of the aforedescribed United States patent to Archie Hood. For purposes of illustration the following is a specific example.

To approximately 100 grams of 2-hydroxyethyl methacrylate was added, dropwise, about 120 grams of freshly distilled difluorophoshoric acid ($HPO_2F_2$) and reaction allowed to occur at room temperature, with stirring for approximately 12 hours at about 25° C. A flush of dry nitrogen was maintained during addition and during the 12 hour reaction period. The resulting product was vacuum distilled to remove the excess difluorophosphoric acid. Then the product was freed of any remaining difluorophosphoric acid by the addition of sodium hydroxide to precipitate the sodium salt of the ester, which after separation by filtration, is washed with absolute ethyl alcohol to remove impurities. The free ester can be regenerated from its sodium salt by mineral acid addition followed by extraction with acetone.

As has already been indicated, the preferred tooth cavity lining compositions of this invention comprise a mixture of the polymerizable organic ester of the monofluorophosphoric acid with other ingredients. These additional ingredients include the following: (1) resin binder, i.e. additional polymerized or polymerizable organic compound; (2) finely divided filler or pigment material; and (3) catalyst for the polymerizable organic monofluorophosphate and for the additional polymerizable material. Still further, the lining composition should preferably include minor amounts of other ingredients such as stabilizers, levelling agents and brighteners. The following specific liner composition, along with explanation of the function of the various ingredients, will serve to illustrate, all percentages being by weight.

A. Resin binder and related ingredients - approximately 18% of the total solids and consisting essentially of:
 1. a mixture of 47% bis (2-methacryloxethyl) isophthalate, 38% bis (2-methacryloxyethyl) phthalate and 15% bis (2-methacryloxyethyl) terephthalate.
 2. monomeric methyl methacrylate - to reduce viscosity, 10% of 1. above.
 3. dodecyl mercaptan — as a polymerization accelerator, 0.5% of 1.
 4. methacrylic acid — as a stabilizer, 0.3% of 1.
 5. 2, 6-di-tertiary butyl p-cresol — as a stabilizer, 0.2% of 1.
 6. N, N, diemthyl 3, 5 dimethylaniline — as a polymerization accelerator, 0.7% of 1.
 7. dimethylpolysiloxane — as a levelling agent, 5 ppm based on 1.
 8. glycerol diemethacrylate monofluorophosphate, 10% based on 1.
 9. gamma — methacrypropyltrimethoxysilane - 0.5% based on 1.

B. Finely divided solid material as pigment and filler, approximately 82% of the total solid material and consisting essentially of:
 1. Finely divided quartz powder, 5 micron or less particle size.
 2. Titanium dioxide, magnesium oxide and calcium oxide, in approximately equal proportions — as a brightener, 3% of 1. (i.e. the quartz powder).

C. Solvent consisting of a mixture, in equal molar amounts of acetone and chloroform, sufficient to provide a pastelike viscosity to the liner composition.

D. Benzoyl Peroxide, as polymerization catalyst, about 1% based on 1, 2 and 8 of Part A.

In practice the catalyst, i.e. part C, is mixed with the solid ingredients which constitute part B and the solvent can be mixed with either Part A or part B whereby there is a two part mix which, upon mixing, commences to polymerize. These two parts can be encapsulated in a two-compartment encapsulation, of appropriate size to be accommodated in mixers well known in the art of dentistry. Hence, the two parts can be most thoroughly mixed by the dentist just prior to application to the tooth cavity.

It will be understood, of course, that the above constitutes a very specific example of a composition embodying the invention and that various of the ingredients can be excluded and, alternatively, additional ingredients can, if desired, be included. Typical of the latter would be the inclusion of an ultraviolet light absorber, such as 2-hydroxy-4-methoxy benzophenone, to prevent yellowing. In accordance with the invention, the key ingredient is, of course, the ester of the monofluorophosphate, and it should be noted that it need only be present in relatively small percentage of the total resin or polymerizable solids of the composition - as little as one percent of the resin solids being sufficient to provide significantly increased bonding. As further points of particular note in conjunction with the above specific example, the quartz powder functions as a strengthening filler having a coefficient of thermal expansion which is such that the coefficient of thermal expansion of the aggregate of the solid ingredients in the liner material substantially matches the coefficient of thermal expansion of the tooth. The quartz powder can preferably be treated with a silane to provide a surface on the quartz particles to increase the bond strength thereof and the resin. Such treatment of quartz, as a filler, is already known in the dental art. Also already known in the dental art is the use of silanes, such as gamma-methacryloxypropyltrimethoxysilane in dental fillings as keying or coupling agents. Reference has been made above to patents teaching such silanes for use in dental fillings. By "keying" or "coupling" agent is meant an ingredient which increases the bond strength of the dental filling and, on this basis, the polymerizable organic phosphoryl monofluoride ingredient in the composition of the present invention could be considered as a substitute, though an improved substitute, for the silanes previously known for this purpose. It bears mention, however, that best results with the present invention have thus far been attained by using the organic phosphoryl monofluoride, in accordance with the present invention, in combination with the silanes heretofore used as coupling or keying agents in that, when the combination is used, there appears to be a synergistic affect. Though, as will be elaborated upon hereinafter, I do have a theory as to the excellent results attainable by way of the use of the polymerizable organic phosphoryl monofluorides, I do not purport to have an explanation for the synergistic effect when such phosphoryl monofluorides are used in combination with the silanes.

Also worthy of mention is the use of the polymerizable organic phosphoryl monofluorides in combination with other compounds used as keying agents, examples being N-phenyl glycine glycidyl methacrylate and the compounds disclosed in U.S. Pat. No. 3,200,142 to R. L. Bowen.

It should be understood that various other resins can be used in place of those, and the combination of those, specified in sub-paragraph 1 of paragraph A above in the specific example. Illustrative of the numerous possibilities are ethylene dimethacrylate, tetraethylene glycol, epoxy resin and polyurethane resin. The key point is that the polymerizable organic phosphoryl monofluoride, which constitutes the principal feature of the present invention, can best be used in combination with other polymeric materials rather than as the sole polymeric material which is applied to the tooth tissue. I also wish to reiterate that whereas it is preferred to incorporate the polymerizable phosphoryl monofluoride only in the liner composition which is applied to the tooth tissue, and then fill the remainder of the cavity with conventional resinuous compositions already known in the dental art, it is within the purview of the invention to formulate the entire filling to include the polymerizable organic phosphoryl monofluoride.

To further elaborate on what has been stated above, in the preferred practice of the method of this invention, the liner composition, including the polymerizable organic phosphoryl monofluoride, is first applied to the entire surface of the tooth cavity, after decayed material has been removed and there has been thorough cleansing, and then, after evaporation of the solvent ingredients, the remainder of the cavity is filled with other resinous composition as described above and is as well known in the art. Where this resinous material used to fill the remainder of the cavity itself contains polymerization catalyst effective to cause polymerization of the polymerizable material of the liner, it is not essential to include catalyst in the liner composition since the catalyst in the bulk of the resinous filling is sufficient to cause the polymerization not just of the bulk of the filling but also of the liner. However, for optimum control, and also flexibility in the choice of the material used for filling the bulk of the cavity, it is preferred that polymerization catalyst for the liner be included in the liner composition itself so that the liner composition is self catalyzing whereby polymerization of the liner is assured independent of any catalyzed polymerization of the remainder of the cavity filling.

I have indicated above that the quartz ingredient performs a function, in addition to that of adding strength, in tending to match the coefficient of thermal expansion of the liner to that of the tooth. But much preferred as a filler, in this regard, is lithium aluminum silicate (which can be in one or more of its geologic forms such as beta-eucryptite, beta-spodumene, petalite, etc.) which have a negative coefficient of thermal expansion and, hence, the amount of which included in the composition can be adjusted such that, in combination with the amounts and the coefficients of thermal expansion of the other solid ingredients of the lining, the coefficient of thermal expansion of the aggregate lining composition can be caused to very closely match that of the tooth.

It will be understood, of course, that particularly where the polymerization catalyst is included as an ingredient in the liner composition, final mixing of the liner composition should only take place just prior to application of the liner to the tooth. Ideally, and as will be appreciated by those skilled in the art of polymer chemistry, the liner composition should be applied and then, after only sufficient time is given to allow substantially total evaporation of the solvent in the liner mixture, the remainder of the cavity is filled with the other polymerizable filling composition, whereupon there can be simultaneous polymerization of the liner and the bulk of the filling composition, by way of the attainable controlled timed catalysis, such that there results the desired copolymerization and cross linking between the liner, which constitutes the transitional layer, and the bulk of the filling.

I do not purport to know all of the precise theory which would explain the success of the invention in providing such excellent bond strength with the tooth structure. However, based on my present theory, and the test results obtained, I believe that the function of the key ingredient of the liner can best be described by denominating this key ingredient as a surface-active comonomer. By this term I mean that the polymerizable ester of the monofluorophorophosphoric acid is a molecule one end of which is non-polar, and organophillic, and capable of copolymerization or homopolymerization, and the other end of which is a polar group which renders the molecule surface active and attracted, for good bond strength, with the calcium phosphate, hydroxyapatite, of the tooth tissue. It is this attraction which may be described as adsorption which results in the adhesion of molecules to a surface. It is not yet known whether the excellent bonding at the interface between the tooth and the lining is a hybrid ionic-covalent oxane bond between the apatite and the ester of hydrogen bonding between polar groups at the interface surfaces. By either theory, however, there would likely be an equilibrium making fluoride ion available as a means of strengthening adjacent tooth structure. But the key point is that by way of the polar fluorophosphate group at one end of the molecule there is excellent adsorption to the tooth tissue resulting in bonding while the polymerizable group at the other end of the molecule results in excellent bonding with the remainder of the tooth filling. The end result is a non-toxic tooth filling which, at one and the same time, provides excellent assurance, by way of the good bond strength, against leakage between the filling-to-tooth tissue interface, which assures against additional tooth caries and which closely matches the tooth tissue in physical properties of both a functional nature and an esthetic nature.

In all of the above I have sought to indicate that in my recommendation as to the practice of this invention, by reference to what I consider preferred embodiments, I have limited myself on the basis of test results to date. Hence, for example, I have indicated that on the basis of conceivable toxicity problems, there could be difficulty in the free substitution of the hydrogen, for example, with other atoms, or combinations of atoms, in the organic radical of the polymerizable phosphoryl monofluoride. On a like basis, and following a similar conservative approach, I have limited by description to the mono esters of fluorophosphoric acid since, to date, time limitations have imposed on me the inability to determine the possible applicability of the di esters of fluorophosphoric acid for the intended purpose as aforesaid. Still further, whereas test results to date indicate that the organic radical of the ester of the fluorophosphoric acid must, for the liner or tooth filling, constitute a polymerizable organic group, and, on the basis of theoretical consideration, I conclude that polymerization of the organic radical, and hence the ability thereof to copolymerize and cross link, constitutes an important feature of the invention, I do not, on the basis of my work to date, desire to necessarily limit the scope of my invention to these features. Still further, whereas to date I have only worked with the free monoesters of monofluorophosphoric acid and not with the sodium, potassium, or other salts of such acids, nevertheless the salts can, it is expected, be used if desired and intended to be comprehended by my invention. Hence whereas I have described my invention with reference to preferred embodiments thereof, it should be appreciated that various changes and modifications may be made, and yet within the purview of my invention as defined in the claims which follow.

The embodiments of the invention in which an exclusive property or privilege is claimed are defined as follows:

1. A composition for bonding to tooth or bone tissue comprising a mixture of an organic phosphoryl monofluoride having the structural formula

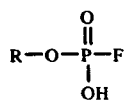

wherein R is an unsaturated aliphatic addition-polymerizable group, and a material selected from the group consisting of the organic polymers, organic compounds capable of polymerization, and mixtures thereof.

2. A composition as set forth in claim 1 wherein said composition also includes a catalyst to cause polymerization.

3. A composition as set forth in claim 1 wherein said composition also includes a silane.

4. A composition as set forth in claim 1 wherein said composition also includes dimethylpolysiloxane.

5. A composition as set forth in claim 1 wherein said composition also includes a finely divided solid material.

6. A method as set forth in claim 5 wherein said finely divided material consists at least in part of lithium aluminum silicate having a negative coefficient of thermal expansion.

7. A composition as set forth in claim 1 wherein said organic phosphoryl monofluoride contains at least one methacrylic group.

8. A composition as set forth in claim 7 wherein said organic phosphoryl monofluoride is glycerol dimethacrylic phosphoryl monofluoride.

9. A composition as set forth in claim 1 wherein said organic radical includes at least one methacrylic group and wherein said other material in said composition also includes methacrylic groups.

* * * * *

UNITED STATES PATENT OFFICE
CERTIFICATE OF CORRECTION

Patent No. 3,997,504  Dated December 14, 1976

Inventor(s) Richard W. Plymale

It is certified that error appears in the above-identified patent and that said Letters Patent are hereby corrected as shown below:

Column 1, line 65, at the right-hand end of the formula set forth, "P" should be --F--.

Column 3, line 50, at the right-hand end of the formula set forth, "P" should be --F--.

Column 3, line 63, at the right-hand end of the formula set forth, "P" should be --F--.

Signed and Sealed this

Twenty-ninth Day of March 1977

[SEAL]

Attest:

RUTH C. MASON
Attesting Officer

C. MARSHALL DANN
Commissioner of Patents and Trademarks